United States Patent
Böhm et al.

(10) Patent No.: US 8,126,248 B2
(45) Date of Patent: Feb. 28, 2012

(54) PROCEDURES FOR THE PRESENTATION OF MEDICAL IMAGES

(75) Inventors: Stefan Böhm, Oberasbach (DE); Peter Durlak, Erlangen (DE); Boris Stowasser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 798 days.

(21) Appl. No.: 12/284,979

(22) Filed: Sep. 26, 2008

(65) Prior Publication Data
US 2009/0097732 A1    Apr. 16, 2009

(30) Foreign Application Priority Data
Sep. 28, 2007  (DE) .................. 10 2007 046 941

(51) Int. Cl.
*G06K 9/00* (2006.01)

(52) U.S. Cl. ............. 382/132; 382/131; 382/260; 378/4

(58) Field of Classification Search .................. 382/131, 382/132, 260; 378/4
See application file for complete search history.

(56) References Cited

U.S. PATENT DOCUMENTS

| | | | |
|---|---|---|---|
| 4,707,786 A * | 11/1987 | Dehner ............................ 378/14 |
| 4,907,156 A * | 3/1990 | Doi et al. ....................... 382/130 |
| 5,461,655 A | 10/1995 | Vuylsteke et al. |
| 5,481,269 A * | 1/1996 | Imhoff et al. .................... 342/90 |
| 5,666,434 A * | 9/1997 | Nishikawa et al. ............ 382/128 |
| 5,708,693 A * | 1/1998 | Aach et al. ....................... 378/62 |
| 6,415,049 B1 * | 7/2002 | Yanagita et al. ............... 382/132 |
| 6,829,323 B2 * | 12/2004 | Toth et al. .......................... 378/4 |
| 6,934,421 B2 * | 8/2005 | Gindele et al. ................ 382/260 |
| 6,943,920 B2 * | 9/2005 | Edgar ........................... 358/3.26 |
| 7,248,749 B2 * | 7/2007 | Avinash et al. ................ 382/260 |
| 7,254,261 B2 * | 8/2007 | Avinash et al. ................ 382/132 |
| 7,362,845 B2 * | 4/2008 | Ning .................................. 378/4 |
| 7,706,497 B2 * | 4/2010 | Hsieh et al. ........................ 378/5 |
| 7,995,066 B2 * | 8/2011 | Bohm et al. ................... 345/475 |
| 2006/0120507 A1 | 6/2006 | Brunner et al. |

FOREIGN PATENT DOCUMENTS

| | | |
|---|---|---|
| DE | 100 10 279 A1 | 9/2001 |
| DE | 693 31 719 T2 | 2/2002 |

* cited by examiner

*Primary Examiner* — Alexander H Taningco (57) ABSTRACT

The invention relates to a method for presentation of medical images by a reproduction facility of a diagnostic device with suppression of the noise with the following steps: one-off calibration of the signal-dependent noise; separation of the signal and noise components in the image; adaptation of the two components according to set parameters; and composition of the signals.

16 Claims, 4 Drawing Sheets

PROCEDURES FOR THE PRESENTATION OF MEDICAL IMAGES

CROSS REFERENCE TO RELATED APPLICATIONS

This application claims priority of German application No. 10 2007 046 941.3 filed Sep. 28, 2007, which is incorporated by reference herein in its entirety.

FIELD OF THE INVENTION

The invention relates to a method for presentation of medical images by a reproduction facility of a diagnostic device with suppression of the noise, as well as to an x-ray diagnostic device for executing the method.

BACKGROUND OF THE INVENTION

Figure 1:
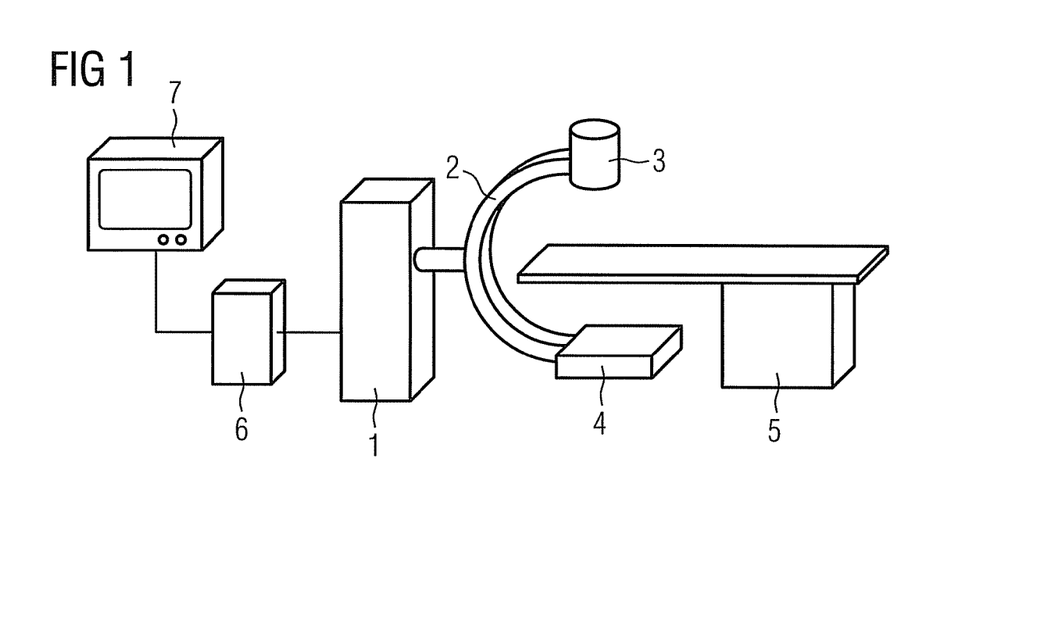
FIG. 1 a known x-ray diagnostic device for carrying out the method.

US 2006/0120507 A1 discloses such an x-ray diagnostic device for executing the method for angiography, which is shown for example in FIG. 1, which features a C-arm 2 supported to allow it to rotate on a stand 1, at the ends of which an x-ray radiation source, for example an x-ray emitter 3, and an x-ray image detector 4 are arranged.

The x-ray image detector 4 can be a rectangular or square flat semiconductor detector, which is preferably made of amorphous silicon (a-Si).

Located in the optical path of the x-ray emitter 3 is a patient support table 5 for recording images for example of a heart of a patient to be examined. Connected to the x-ray diagnostic device is an imaging system 6 which receives and processes the image signals of the x-ray image detector 4. The x-ray images can then be viewed on a monitor 7.

During recording of such 2D data x-ray images are frequently produced which have a very high amount of noise and in which the signal-to-noise ratio is thus also bad. This can make diagnosis more difficult.

Figure 2:
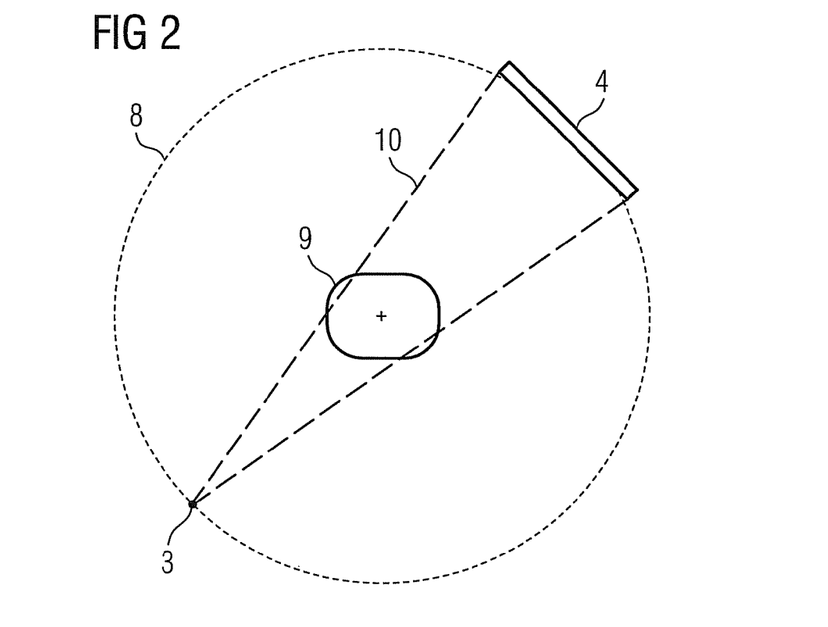

If 3D data sets are to be created, the rotatably-supported C-arm 2 with x-ray source 3 and x-ray detector 4 is turned, so that, as shown schematically in FIG. 2 looking down on the axis of rotation, the x-ray source 3 shown in this diagram by its beam focus 3 as well as the x-ray image detector 4 move around an object 9 to be examined on a planetary track 8. The planetary track 8 can be followed completely or partly for creating a 3D data set.

The object 9 to be examined can for example be the body of an animal or a human being, but can also be a phantom body.

The x-ray source 3 emits a ray bundle 10 emanating from the ray focus of its radiographic source, which hits the x-ray image detector 4.

The x-ray source 3 and the x-ray image detector 4 thus each circulate around the object 5, so that the x-ray source 3 and the x-ray image detector 4 lie on opposite sides of the object 9 in relation to each other.

In normal radiography or fluoroscopy using such an x-ray diagnostic device the medical 2D data of the x-ray image detector 4 will be buffered in the imaging system 6 if necessary and subsequently reproduced on the monitor 7.

Figure 3:
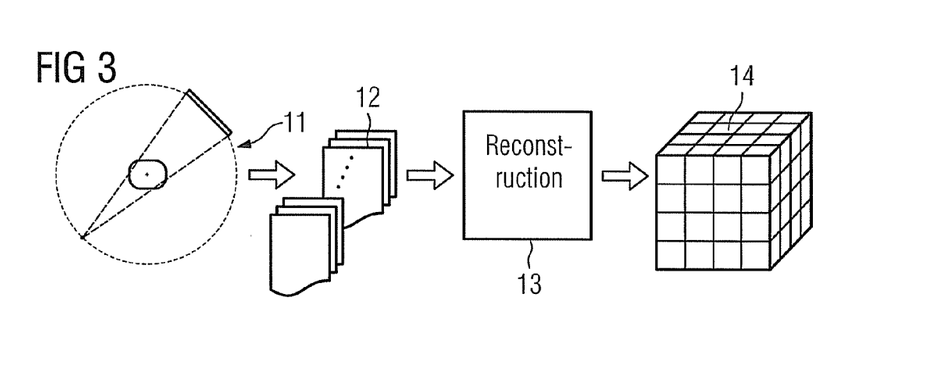

FIG. 3 now shows the known execution sequence for recording 3D-data which is created by means of an x-ray device 11 described in FIGS. 1 and 2. The raw data 12 is fed to a reconstruction 13, which computes from it the volume data set or 3D data set 14.

In the creation of such 3D data, the reconstruction can be adversely affected as a result of noise in the raw data, which leads to a reduction in the ability to detect contrasts and structures in the 3D data set.

In a reconstruction of the 3D data, said data comprises a data set containing density information of the location (x, y, z) for example. This density information can now contain a noise component which reduces the 3D image quality.

The only option available to the doctor for increasing the signal-to-noise ratio (S/N ratio) and thus the image quality is to increase the dose, but this results in both the patient and the doctor being subjected to a higher exposure to radiation. There are also statutory regulations restricting the maximum dose.

Although the S/N ratio can be improved by a smoothing filter, for example Crispyl, which finds edges in the image and smoothes the image along these edges, a meaningful noise reduction is not guaranteed by this.

SUMMARY OF THE INVENTION

The object underlying the invention is to embody a method and a device of the type stated at the outset such that effective noise reduction can be brought about in a simple manner both for 2D and also 3D images.

The object is inventively achieved for a method through the following steps:
a) One-off calibration of the signal-dependent noise,
b) Separation of the signal and noise components in the image,
c) Adapting the two components in accordance with parameters that have been set and
d) Composing the signals.

The separate processing of the signal and noise components enables the noise components to be at least reduced in a simple and effective manner.

It has proved to be advantageous for the separation of the image components to be undertaken by a filter with non-linear wavelet decomposition.

The method can advantageously feature the following steps:
S1) One-off calibration of the signal-dependent noise,
S2) Decomposition of the image into bandpass images,
S3) Use of a local signal estimator for determining the local signal component in the image,
S4) Adapting the local signal strength as a function of the local measured signal strength and of the calibrated noise component and
S5) Reconstruction of the image.

According to the invention the one-off calibration in accordance with step a) or S1 can depend on local frequency and intensity.

Especially advantageously the one-off calibration in accordance with step a) or S1 can be a signal-dependent calibration of the quantum noise and of the electrical noise.

It has been shown to be advantageous for the decomposition of the image into bandpass images in accordance with step S2 to be carried out by means of non-linear lowpass filters of different frequencies, the output signals of which are subtracted from one another.

In an advantageous manner the local signal component in accordance with S3 can be made up of a noise signal and a useful signal.

Especially advantageously the local signal estimator can be a local kernel which determines the standard deviation (ó) in this kernel, so that the total standard deviation ($\sigma_{total}$) can be measured and the $\sigma_{signal}$ standard deviation a signal can be estimated as a result of the standard deviation of the noise component ($\sigma_{noise}$) known from the calibration.

Inventively the method steps can be applied to 2D data or 3D data, with the method being applied to raw data reconstructed after filtration into a volume data, or alternatively applied to volume data which is composed after filtering into a volume data set.

The object is inventively achieved for a device by the image system having a device for noise calibration, a noise filter which separates the image signal into useful signal and noise signal, a correction stage which adapts these two components in accordance with set parameters and a reconstruction stage which assembles the data into a data set.

The result able to be achieved is that 2D or 3D data sets are separated according to frequency, filtered separately and corrected as well as subsequently composed, so that at least one noise-reduced data set is obtained.

In an advantageous manner the noise filter can separate the image signal, using a non-linear wavelet decomposition, into useful signal and noise signal.

It has been shown to be advantageous for the noise filter to be a 3-dimensional noise filter which separates a volume data set into bandpass volume data using a non-linear lowpass filter.

BRIEF DESCRIPTION OF THE DRAWINGS

The invention is explained below in greater detail on the basis of the exemplary embodiments shown in the drawing. The figures are as follows:

FIG. 2 a view of the track of a detector and a radiographic source around an object to be examined in a view along the axis, FIG. 3 a schematic diagram of a known overall sequence, FIG. 4 a schematic diagram of a first inventive overall sequence, FIG. 5 a schematic diagram of a further inventive overall sequence, FIG. 6 an inventive method sequence, FIG. 7 a step phantom for calibrating the x-ray diagnostic device in accordance with FIG. 1, FIG. 8 a section from an x-ray image of a step phantom, FIG. 9 a inventive embodiment with bandpasses and FIG. 10 an inventive embodiment implemented with lowpasses.

DETAILED DESCRIPTION OF THE INVENTION

Figure 4:
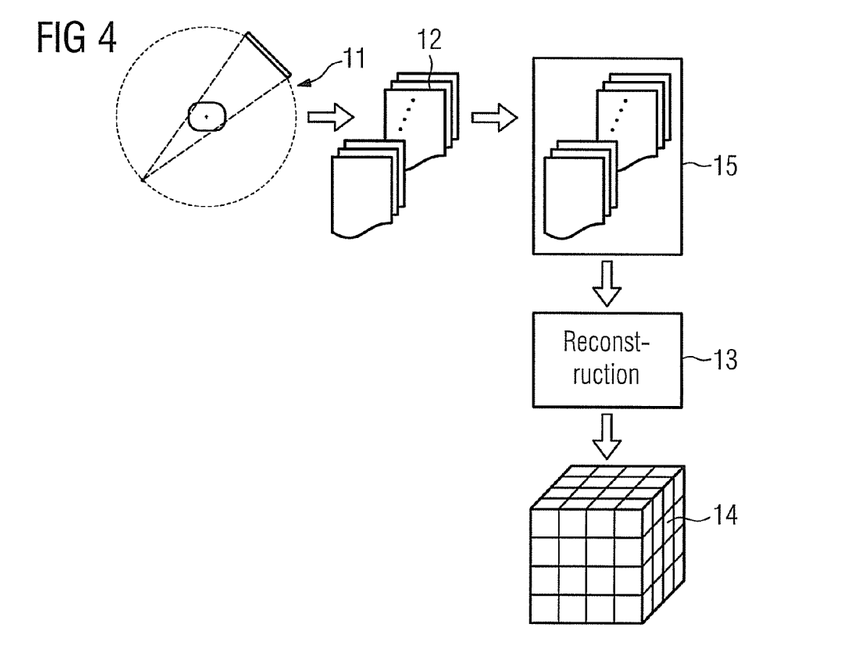

FIG. 4 now shows schematically the inventive execution sequence of the recording of 3D data, which is created by means of the x-ray device 11 described in FIGS. 1 and 2. The raw data 12 is first subjected to a noise filtering 15 of the raw data 12 and then fed to the reconstruction 13, which calculates the volume data set or 3D data set 14 from it.

Figure 5:
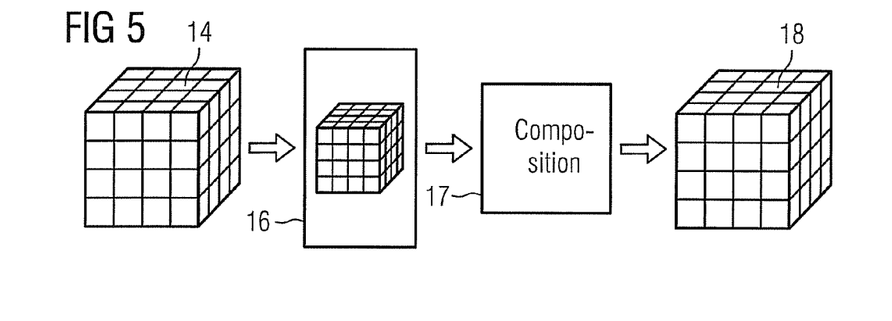

FIG. 5 is a schematic diagram of a further inventive execution sequence of the processing of 3D data which is created by an x-ray device 11 described in FIGS. 1 and 2 and has been processed in accordance with the execution sequence depicted in FIG. 3. The 3D-data record 14 is subjected to noise filtering 16 and then fed to a composition 17 which computes the filtered 3D data record 18 from this.

Figure 6:
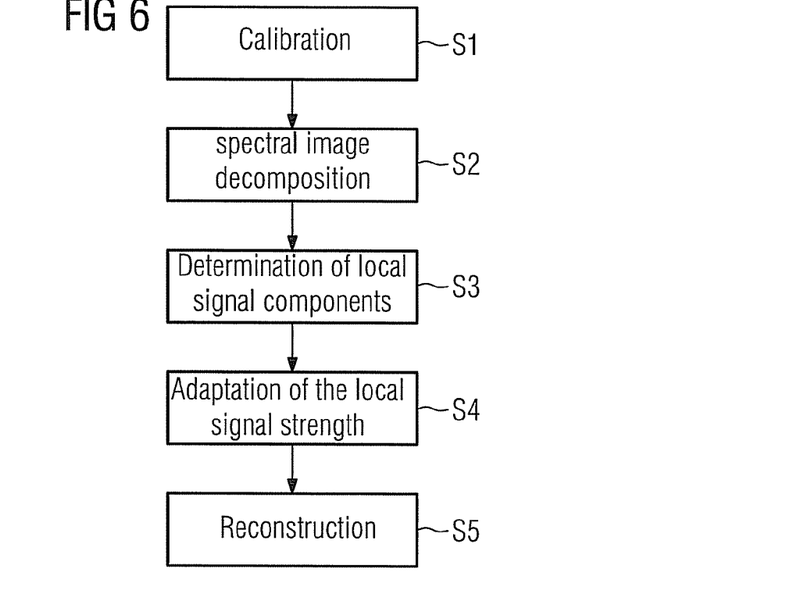

FIG. 6 provides a more detailed description of the execution sequence of the filtering method. In step S1 a one-off, especially local-frequency-dependent and intensity-dependent calibration of the signal-dependent noise, for example of the quantum noise and of the electrical noise, is performed. Subsequently in step S2 the image is separated into bandpass images, typically using nonlinear lowpass filters. In step S3 a local signal estimator is used to determine the local signal component which comprises a noise component and a useful signal component. In step S4 the local signal strength is adapted depending on the local measured signal strength and the calibrated noise component. Finally in step S5 the image is reconstructed by additive composition.

The signal estimator is a local kernel, for example here 3×3, which defines the standard deviation (ó) in this kernel. This allows the total standard deviation ($\sigma_{total}$ to be measured; the standard deviation of the noise component ($\sigma_{noise}$) is known from the calibration and this allows the signal standard deviation $\sigma_{signal}$ to be estimated.

The filter method for noise removal, the suppression of the noise, consists of the following steps:

One-off local frequency and intensity-dependent calibration of the signal-dependent quantum noise and of the electrical noise, S1) Separation of the image into bandpass images using non-linear lowpass filters, S2) Use of a local signal estimator for determining the local signal component made up of a noise component and a useful signal, S3) Adapting the local signal strength depending on the local measured signal strength and the calibrated noise component and S4) Reconstruction of the image.

The filter method is based on separating the image into individual bandpass images. A wavelet decomposition is used, in which the number of bandpass coefficients is identical to that of the input image.

To compute the lowpass images an unsharp filter is used, the kernel of which is enlarged in accordance with band by the insertion of holes.

The difference between two consecutive lowpass images produces the bandpass image.

If $l_0$ is the input image and $l_{i+1}$ the lowpass-filtered image of $l_i$, then the bandpass image $h_i$ defined as:

$$h_i = l_i - l_{i+1}$$

for $i \geq 0$.

There now follows a precise description of the method steps for the 2D imaging:

Decomposition of the images into bandpass images using a non-linear lowpass filter An image pixel is referred to below as I(x, y), with (x, y) being the coordinates of the pixel.

A 2D window (3×3) around the central pixel (x, y) is considered. This window consists of the pixels (x',y'), with $|x'-x| \leq 1, |y-y'| \leq 1$. This window is used to compute the filtered value I'(x, y). This operation occurs for all pixels of the image matrix.

The individual filtered pixel values are defined as follows

In the first step all values of the 2D window are transferred into a one-dimensional field:

$$x_K = (x_1, x_2, \ldots, x_N)^t$$

In this example N=9.

Al pixels are now sorted in the field $x_K$ according to their difference from I(x, y) and a new 1D field is obtained:

$$x_k = (x_{(1)}, x_{(2)}, \ldots, x_{(N)})^t,$$

with $x_{(1)} = I(x, y)$ being the central pixel in the 2D window is, and $x_{(i)}, i=2 \ldots N$ with $|x_{(1)} - x_{(i)}| \leq |x_{(1)} - x_{(j)}|, j=i \ldots N$.

The second step consists of the filtering. The filtered pixel value is computed as follows:

$$y = a^t x_k / \gamma = \frac{1}{\gamma} \sum_{i=1}^{N} a_i x_{(i)}$$

With $a=(a_1, a_2, \ldots, a_N)^t$: Weighting factors and $$\gamma = \sum_{i=1}^{N} a_i.$$

Here $a_i=1$ is used for $i=1 \ldots M$ and $a_i=0$ for $i>N$. This implies $\gamma=M$.

The value M and thus also $\gamma$ are parameters and describe the smoothing of the decomposition.

After the image has been filtered by the above steps and the band $1_{m=0}$ created in this way, the band $1_{m+1}$ is recursively created. This is done by enlarging the kernel, i.e. the coordinates $x \cdot 2^m$, $y \cdot 2^m$ with $x \in \{-1; 0; 1\}$ and $y \in \{-1; 0; 1\}$ are now used for the window with the filtered data from $1_m$.

These operations are executed recursively until m=4.

The bandpass-filtered image of the step m is computed as follows:

$$h_m = l_m - l_{m+1}.$$

Determination of the Calibrated Noise Values

Let the dynamic range of the detector have n elements $[0, \ldots, n-1]$, onto which the intensity values are mapped in a linear fashion. Through the step phantom 21 depicted in FIG. 7, to which unattenuated x-ray radiation 20 is applied, the calibrated noise components are now determined.

Figure 7:
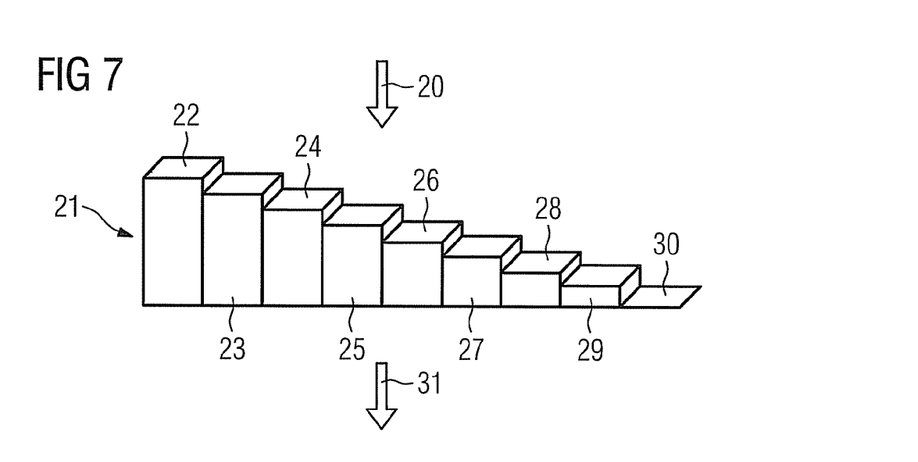

Practice has shown that a subdivision of the dynamic range into eight steps 22 to 29 is sufficient; however a finer subdivision can be used.

The material of the step phantom can be Pb, Cu or aluminum.

The following steps of absorption of the input signal must be present (+5%):

Step 22 features the full absorption of 100%, step 23 typically of 87.5%, step 24 of 75%, step 25 of 62.5%, step 26 of 50%, step 27 of 37.5%, step 28 of 25%, step 29 of 12.5% and an unattenuated surface 30 no absorption (0%).

The surfaces of the steps 22 to 29 must be adapted, that with four bandpasses a $(2*2*2^{4-1}=)$ 64 times 64 pixel homogeneous surface is available for calibration. The x-ray radiation 31 attenuated by the step phantom 21 is detected by the x-ray image detector 4.

Figure 8:
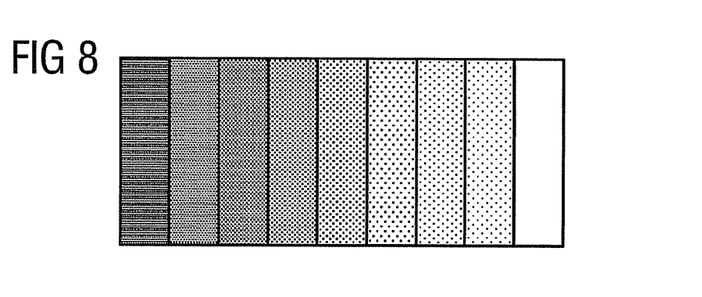

FIG. 8 shows a section from a recorded x-ray image of a step phantom 21 in accordance with FIG. 3.

The data record is separated into its bandpass images $h_m$ and lowpass images $l_m$ and the intensity-dependent noise values (I) are determined within the various absorption surfaces for the respective band:

$$\sigma_{noise}^m(I^{mn}, x, y) = \sum_{i=-2}^{2} \sum_{j=-2}^{2} |h_m(x+i, y+j) - h_m(x, y)|;$$

The nth (here n=1 . . . 8) intensity $I^{mn}$ of the band m is measured from the lowpass image $l_{m+1}$ at the coordinates (x, y):

$$I^{mn} = l_{m+1}(x, y);$$

From the discrete measured intensities with the associated noise values the missing intensities of the dynamic range with their noise values are determined by interpolation. To do this splines are applied for example through the eight measured points.

Specific functions are identified as splines. An nth-degree spline is a function which is composed in sections from polynomials with maximum degree n. In this case at the points at which two polynomial sections join, the so-called node, specific conditions are imposed, for example that the spline is always able to be differentiated (n−1) times.

Splines are used for interpolation. By being defined in sections splines are more flexible than polynomials and still relatively simple and smooth.

If the spline involves a sectional linear function, the spline is referred to as linear (a polygon shape is then involved); in a similar way there are square, cubic etc. splines.

Adapting the Bandpass Coefficients Using a Local Signal Estimator and the Calibrated Noise Values The coefficient in the decomposition is composed depending on the non-linear decomposition additively from a signal component and a noise component. The above-mentioned signal estimator allows the factor to be estimated with which the set of coefficients must be reduced in order to get rid of the noise component. This factor is $f=(\sigma_{total} - \sigma_{noise})/\sigma_{total}$. The bandpass coefficient is now multiplied by this factor.

The bandpass coefficients are also adapted to the calibrated noise component and the signal ($\sigma_{signal}$) measured by the local signal estimator which is composed of a noise component and a signal component.

The following assumption is used as a starting point:

The overall signal in a bandpass is composed of a useful signal and a noise component:

$$\sigma_{total}^m(x,y) = \sigma_{signal}^m(x,y) + \sigma_{noise}^m(I);$$

The overall signal can be measured:

$$\sigma_{total}^m(x, y) = \sum_{i=-2}^{2} \sum_{j=-2}^{2} |h_m(x+i, y+j) - h_m(x, y)|;$$

The intensity is measured in this case from the lowpass image $l_{m+1}$ at the coordinates (x, y):

$$I = l_{m+1}(x, y);$$

The factor $f_m$, by which the overall signal must be multiplied in order to obtain the useful signal, is:

$$f^m(x, y, z) = \frac{\sigma_{total}^m(x, y, z) - \sigma_{noise}^m(I)}{\sigma_{total}^m(x, y, z)};$$

The new coefficient of the bandpass m is computed as follows:

$$h'_m(x,y,z) = f_m(x,y,z) \cdot h_m(x,y,z);$$

The image is then reconstructed again from the m=1 . . . n bandpasses:

$$f_{out}(x, y, z) = l_{n+1}(x, y, z) + \sum_{m=0}^{n} h_m(x, y, z).$$

Figure 9:
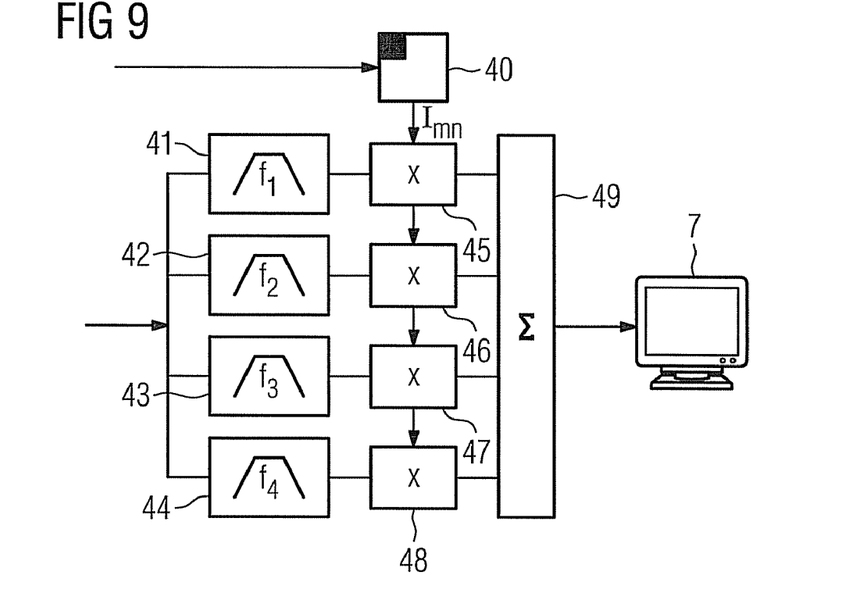

The principle of the processing circuit is shown in greater detail in FIG. 9. The calibration values are read into a memory 40 after completion of calibration (S1). The spectral image decomposition (S2) is undertaken by bandpasses 41 to 44, to which the input signal is fed. The outputs of the bandpasses 41 to 44 are connected to multiplication stages 45 to 48 which adapt the local signal strength (S4) by multiplication of the bandpass signal by the intensity Imn. The outputs of the multiplication stages are connected to an addition stage 49 for reconstruction (S5). The output signal of the addition stage 49 can be displayed via the monitor 7.

Figure 10:
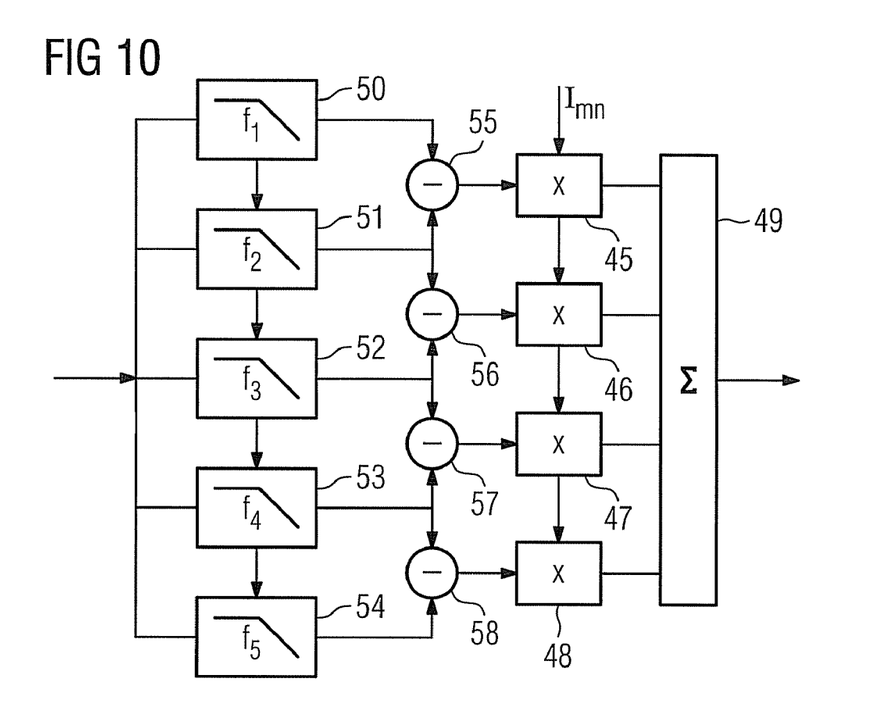

The structure of the processing circuit in accordance with FIG. 10 essentially corresponds to that depicted in FIG. 9. The four bandpasses 41 to 44 have merely been replaced by five lowpasses 50 to 54, the output signals of which are converted by adjacent lowpasses 50 to 54 by subtraction stages 55 to 58 into a bandpass-filtered signal, which is then further processed as a result of the multiplication stages 45 to 48 and addition stages 49 and reproduced by means of the monitor 7.

The method can also be applied to a 3D volume. Here too it is based on a one-off calibration of the noise of the reconstructed volume and of a subsequent 3-dimensional noise filter.

The noise filter includes the following steps:
Separating the 3D volume into bandpass volumes using a non-linear lowpass filter.
Using a local signal estimator for determining the local signal component, which is composed of a noise component and a useful signal.
Adapting the local signal strength depending on the local measured signal strength and the calibrated noise component.
Composition of the volume.
Decomposition of the 3D Volume into Bandpass Volumes For decomposition of the 3D volume a wavelet decomposition is used, in which the number of the bandpass coefficients is identical to that of the input volume.

To compute the lowpass volume an unsharp filter is used, the kernel of which is enlarged in accordance with band by the insertion of holes.

The difference between two consecutive lowpass volumes produces the bandpass volume.

If $l_o$ is the input volume and $l_{i+1}$ is the lowpass-filtered volume of I, then the bandpass volume $h_i$ is defined as:

$$h_i = l_i - l_{i+1}$$

for $i \geq 0$.

In the decomposition step the sum of the absolute deviation from the central pixel of 4 pixels in 11 different directions in the band k is computed:

$$s_1^k(x,y,z) = \sum_{i \in \{-2,-1,1,2\}} |l_{k-1}(x+i\cdot 2^{k-1}, y, z) - l_{k-1}(x,y,z)|$$

$$s_2^k(x,y,z) = \sum_{i \in \{-2,-1,1,2\}} |l_{k-1}(x, y+i\cdot 2^{k-1}, z) - l_{k-1}(x,y,z)|$$

$$s_3^k(x,y,z) = \sum_{i \in \{-2,-1,1,2\}} |l_{k-1}(x+i\cdot 2^{k-1}, y+i\cdot 2^{k-1}, z) - l_{k-1}(x,y,z)|$$

$$s_4^k(x,y,z) = \sum_{i \in \{-2,-1,1,2\}} |l_{k-1}(x+i\cdot 2^{k-1}, y-i\cdot 2^{k-1}, z) - l_{k-1}(x,y,z)|$$

$$s_5^k(x,y,z) = \sum_{i \in \{-2,-1,1,2\}} |l_{k-1}(x, y, z+i\cdot 2^{k-1}) - l_{k-1}(x,y,z)|$$

$$s_6^k(x,y,z) = \sum_{i \in \{-2,-1,1,2\}} |l_{k-1}(x+i\cdot 2^{k-1}, y, z+i\cdot 2^{k-1}) - l_{k-1}(x,y,z)|$$

$$s_7^k(x,y,z) = \sum_{i \in \{-2,-1,1,2\}} |l_{k-1}(x-i\cdot 2^{k-1}, y, z+i\cdot 2^{k-1}) - l_{k-1}(x,y,z)|$$

$$s_8^k(x,y,z) = \sum_{i \in \{-2,-1,1,2\}} |l_{k-1}(x+i\cdot 2^{k-1}, y+i\cdot 2^{k-1}, z+i\cdot 2^{k-1}) - l_{k-1}(x,y,z)|$$

$$s_9^k(x,y,z) = \sum_{i \in \{-2,-1,1,2\}} |l_{k-1}(x+i\cdot 2^{k-1}, y-i\cdot 2^{k-1}, z+i\cdot 2^{k-1}) - l_{k-1}(x,y,z)|$$

$$s_{10}^k(x,y,z) = \sum_{i \in \{-2,-1,1,2\}} |l_{k-1}(x-i\cdot 2^{k-1}, y+i\cdot 2^{k-1}, z+i\cdot 2^{k-1}) - l_{k-1}(x,y,z)|$$

$$s_{11}^k(x,y,z) = \sum_{i \in \{-2,-1,1,2\}} |l_{k-1}(x-i\cdot 2^{k-1}, y-i\cdot 2^{k-1}, z+i\cdot 2^{k-1}) - l_{k-1}(x,y,z)|$$

The minimum deviation is determined from this:

$$S_{min} := \min(S_1^k(x,y,z), S_2^k(x,y,z), S_3^k(x,y,z), S_4^k(x,y,z),\\ S_5^k(x,y,z), S_6^k(x,y,z), S_7^k(x,y,z), S_8^k(x,y,z), S_9^k(x,y,z),\\ S_{10}^k(x,y,z), S_{11}^k(x,y,z))$$

The pixel value of the mth band $I_m(x, y, z)$ is determined from the previous pixel value $I_{m-1}(x, y, z)$ as follows:

$$l_m(x,y,z) = \frac{\sum_{i=-1}^{1}\sum_{j=-1}^{1}\sum_{k=-1}^{1} w_{i,j}^m l_{m-1}(x+i\cdot 2^{m-1}, y+j\cdot 2^{m-1}, z+k\cdot 2^{m-1})}{\sum_{i=-1}^{1}\sum_{j=-1}^{1}\sum_{k=-1}^{1} w_{ijk}^m}$$

The weight $w_{ijk}^m$ of the mth band is calculated as follows:

$$w_{ijk}^m(x,y,z) = \left\{ \frac{1}{\max\left(S_{min}, \left|l_{m-1}(x+i\cdot 2^{m-1}, y+j\cdot 2^{m-1}, z+k\cdot 2^{m-1})\right|\right)} \Big|_{i,j \neq 0}, 0 \Big|_{i,j=0} \right\}$$

The bandpass-filtered volume of stage m is computed as follows:

$$h_m = l_m - l_{m+1}$$

The calibrated noise values are now determined as already described.

The data set is separated into its bandpass volumes $h_m$ and $l_m$ and within the different absorption cubes the intensity-dependent noise values are determined:

$$\sigma_{noise}^m(x,y,z) = \sum_{i=-2}^{2}\sum_{j=-2}^{2}\sum_{k=-2}^{2} |h_m(x+i, y+j, z+k) - h_m(x,y,z)|;$$

The missing intensities of the dynamic range with their noise values are determined by interpolation from the discrete measured intensities with the associated noise values.

Adapting the bandpass coefficients using a local signal estimator and the calibrated noise values The following assumption is used as a starting point:
The overall signal is composed of a useful signal and a noise component:

$$\sigma_{total}^m(x,y,z) = \sigma_{signal}^m(x,y,z) + \sigma_{noise}^m(I);$$

The overall signal can be measured:

$$\sigma_{total}^m(x, y, z) = \sum_{i=-2}^{2} \sum_{j=-2}^{2} \sum_{k=-2}^{2} |h_m(x+i, y+j, z+k) - h_m(x, y, z)|;$$

The factor $f_m$, by which the overall signal must be multiplied to obtain the useful signal, is:

$$f_m(x, y, z) = \frac{\sigma_{total}^m(x, y, z) - \sigma_{noise}^m(I)}{\sigma_{total}^m(x, y, z)}$$

The new coefficient of the bandpass m is computed as follows:

$$h'_m(x,y,z) = f_m(x,y,z) \cdot h_m(x,y,z)$$

The image is then reconstructed again from the n bandpasses:

$$f_{out}(x, y, z) = l_{n+1}(x, y, z) + \sum_{m=0}^{n} h_m(x, y, z)$$

The application of a 3-dimensional noise-reduction filter provides the user with an improved 3D quality.

The proposed method for noise reduction 2D data with the aid of a calibrated noise component allows the noise in medical images to be almost completely eliminated.

This produces the following advantages for the examining physician and the patient Improved 2D image quality:
  Better and faster diagnosis are possible.
Savings in dosage with the image quality remaining the same:
  The exposure to radiation of the doctor and the patient can be reduced while retaining the same image quality.

Upstream connection of a signal-invariant noise filter with the method described above produces the following advantages for 3D applications:

Increase in the 3D image quality through an improved reconstruction by means of noise filters:
  Less noise and better contrast recognition in the reconstructed layers.
Savings in dosage with the image quality remaining the same:
  A reduced-dose imaging protocol with the same image quality can be used for the examiner and the patient.
New examinations:
  With very fast image protocols (e.g. 200 images/s):
  Physical limits of x-ray tubes do not allow the required dose to be applied. The increased reconstruction quality makes this option possible for the customer (doctor and patient).
For very long imaging protocols:
  By the introduction of new trajectories (e.g. by robot arm) for example physical limits of current x-ray tubes can be reached. The increased reconstruction quality makes this option possible.

The tomographic imaging device involved in the invention can for example be x-ray C-arm systems, biplanar x-ray devices or computer tomographs.

Instead of the stand 1 shown, floor or ceiling tripods can also be used, to which the C-arms 2 are attached. The C-arms 2 can also be replaced by a so-called electronic C-arm 2, in which there is an electronic coupling of x-ray source 3 and x-ray image detector 4.

The C-arms 2 can also be guided on robot arms which are attached to the ceiling or the floor. The method can also be conducted with x-ray devices, in which the individual, image-generating components 3 and 4 are each held by a robot arm which is arranged on the ceiling and/or floor in each case.

The invention claimed is:

1. A method for presenting a medical image with a suppression of noise, comprising:
   one-off calibrating a signal-dependent noise;
   separating a signal component and a noise component in the medical image;
   adapting the signal component and the noise component according to a set of parameters;
   composing the signal component for the medical image based on the adapted signal component; and
   presenting the medical image;
   decomposing the medical image into a bandpass image;
   measuring a strength of a local signal component in the bandpass image by a local signal estimator;
   adapting a strength of the local signal component depending on the measured strength of the local signal component and the calibrated noise; and
   reconstructing the medical image based on the adapted strength of the local signal component using an additive composition.

2. The method as claimed in claim 1, wherein the signal component and the noise component are separated by a filter with non-linear wavelet decomposition.

3. The method as claimed in claim 1, wherein the one-off calibration depends on a local frequency and a local intensity.

4. The method as claimed in claim 1, wherein the signal-dependent noise comprises a quantum noise and an electrical noise.

5. The method as claimed in claim 1, wherein the medical image is decomposed into the bandpass image by a plurality of non-linear lowpass filters having different filter frequencies.

6. The method as claimed in claim 5, wherein output signals of the non-linear lowpass filters are subtracted from each other.

7. The method as claimed in claim 1, wherein the local signal component comprises a local noise component and a local useful signal.

8. The method as claimed in claim 1, wherein the local signal estimator is a local kernel which defines a standard deviation in the kernel.

9. The method as claimed in claim 8, wherein a total standard deviation is determined based on the standard deviation in the kernel and a signal standard deviation is a function of a noise standard deviation known from the standard deviation in the kernel.

10. The method as claimed in claim 1, wherein the method is applied to 2D data.

11. The method as claimed in claim 1, wherein the method is applied to 3D data.

12. The method as claimed in claim 11, wherein the method is applied to a raw data and reconstructed into a volume data after the filtering.

13. The method as claimed in claim 12, wherein the method is applied to the volume data and reconstructed into a volume data set after the filtering.

14. An x-ray diagnostic device, comprising:
- an x-ray source for creating x-ray radiation;
- an x-ray image detector for detecting the x-ray radiation and converting the x-ray radiation into an image signal comprising an electrical signal sequence;
- an imaging processing device for processing the electrical signal sequence comprising steps of:
  - one-off calibrating a signal-dependent noise;
  - separating the image signal into a useful signal and a noise signal;
  - adapting the useful signal and the noise signal in accordance with a set of parameters;
  - composing the adapted data into an image data record;
  - decomposing the image data record into a bandpass image;
  - measuring a strength of a local signal component in the bandpass image by a local signal estimator;
  - adapting a strength of the local signal component depending on the measured strength of the local signal component and the calibrated noise; and
  - reconstructing the image data record based on the adapted strength of the local signal component using an additive composition.

15. The x-ray diagnostic device as claimed in claim 14, wherein a noise filter separates the image signal through a non-linear wavelet decomposition.

16. The x-ray diagnostic device as claimed in claim 15, wherein the noise filter is a 3-dimensional noise filter that separates a volume data set into a bandpass volume data by a non-linear lowpass filter.

* * * * *